United States Patent [19]
Moll et al.

[11] 3,957,611
[45] May 18, 1976

[54] ATMOSPHERE MONITORING ELECTROCHEMICAL CELL

[75] Inventors: Robert B. Moll, Havre de Grace, Md.; William J. Barrett, Birmingham, Ala.; Eugene R. Kuczynski, Glenside; Earl W. Shaffer, Jr., Warrington, both of Pa.

[73] Assignee: The United States of America as represented by the Secretary of the Army, Washington, D.C.

[22] Filed: Oct. 16, 1968

[21] Appl. No.: 768,560

[52] U.S. Cl. .................. 204/195 B; 204/195 R; 204/195 F
[51] Int. Cl.² ................................ G01N 27/26
[58] Field of Search ............ 204/195, 195 B, 195 F, 204/195 G, 195 R

[56] References Cited
UNITED STATES PATENTS

| | | |
|---|---|---|
| 3,103,480 | 9/1963 | Watanabe et al. .............. 204/195 G |
| 3,151,052 | 9/1964 | Arthur et al. ...................... 204/195 F |
| 3,398,358 | 8/1968 | Bokhoven et al. ................... 204/195 |
| 3,471,393 | 10/1969 | Ingruber ............................. 204/195 |
| 3,496,084 | 2/1970 | Stack, Jr. ............................. 204/195 |
| 3,523,872 | 8/1970 | Hersch et al. .................... 204/195 R |
| 3,586,608 | 6/1971 | Juda et al. ........................ 204/195 R |

*Primary Examiner*—Edward A. Miller
*Attorney, Agent, or Firm*—Nathan Edelberg; Robert P. Gibson; Kenneth P. Van Wyck

[57] ABSTRACT

An electrochemical cell and method for monitoring toxic compound atmospheric contamination comprising a coiled measuring electrode means, an elongated reference electrode means, a reaction chamber means, an oxime electrolyte means, and a thermal compensating network means; said cell being connected to an electric circuit and alarm means to monitor said contamination.

13 Claims, 9 Drawing Figures

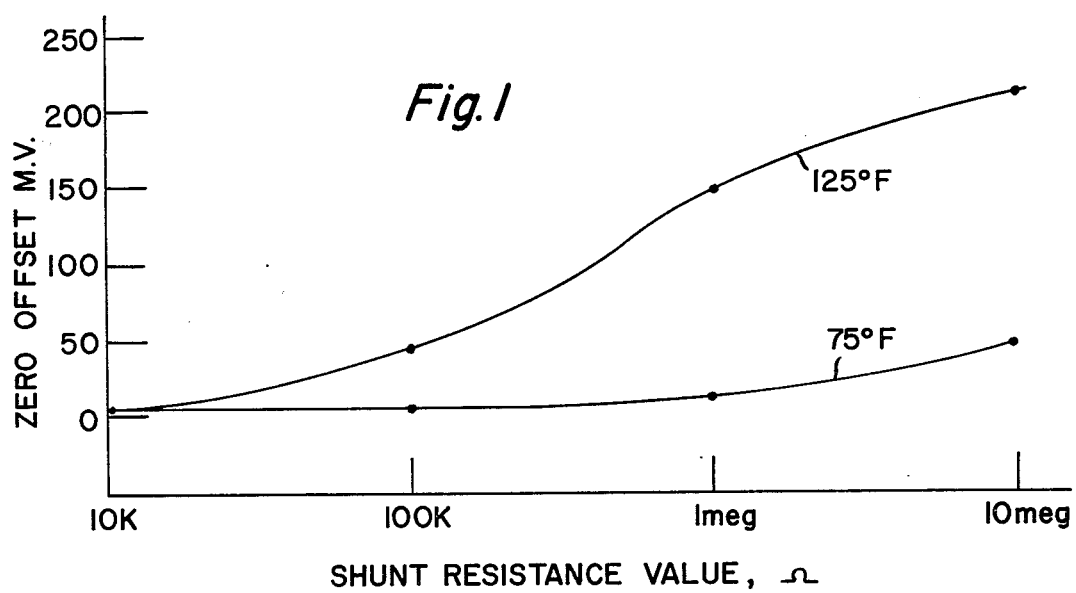
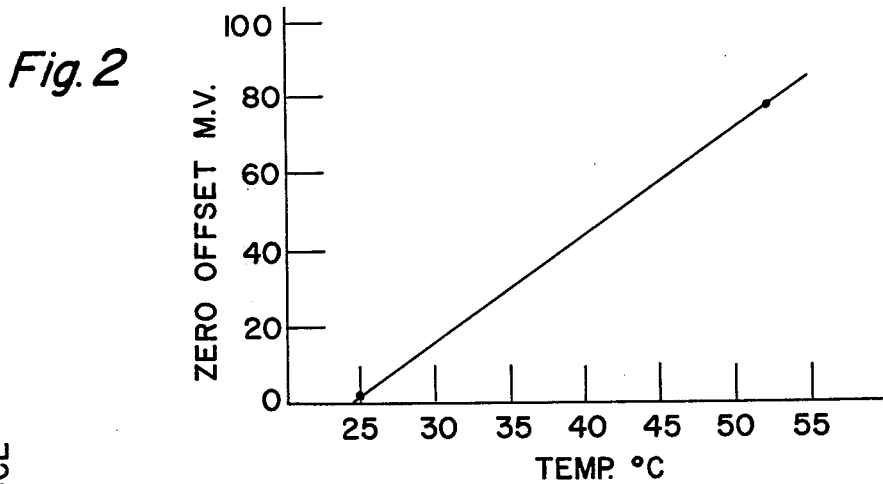
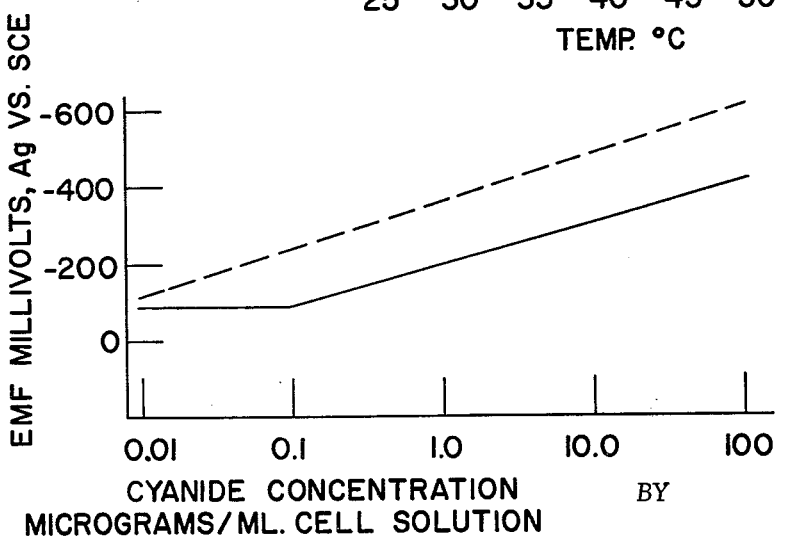
INVENTORS
Robert B. Moll
William J. Barrett
Eugene R. Kuczynski
Earl W. Shaffer Jr.
Harry M. Saragovitz
Edward J. Kelly
Herbert Berl
BY
ATTORNEYS INVENTORS
Robert B. Moll
William J. Barrett
Eugene R. Kuczynski
Earl W. Shaffer Jr.
Harry M. Saragovitz
Edward J. Kelly
Herbert Berl
BY

ATTORNEYS

ATMOSPHERE MONITORING ELECTROCHEMICAL CELL

DEDICATORY CLAUSE

The invention described herein may be manufactured, used, and licensed by or for the Government for governmental purposes without the payment to us of any royalty thereon.

Our invention relates to an electrochemical cell which will rapidly, less than five minutes, detect submicrogram quantities of toxic compounds such as hydrogen cyanide, hydrogen sulfide, phosgene, and G agents, and a compensating network therefor to minimize thermal drift.

Due to the dissemination of toxic compounds such as hydrogen cyanide, hydrogen sulfide, and chemical warfare agents in the atmosphere in industrial plants having hazardous atmospheres and in warfare, techniques and apparatus were necessary to monitor the existence of low concentration, such as $0.2 \times 10^{-6}$ to $0.4 \times 10^{-6}$ grams of contaminant toxic compound per liter of air, hazardous air contaminants. Our invention was conceived and reduced to practice to solve this urgent problem and necessity.

A principal object of our invention is to provide an electrochemical cell for rapidly detecting, less than 5 minutes, a low concentration, $0.2 \times 10^{-6}$ to $0.4 \times 10^{-6}$ grams of contaminant per liter of air, of air contamination.

Another object of our invention is to provide an electrochemical cell for rapidly detecting a low concentration of air contamination by forming a gas/substrate solution interface within the cell to enhance stripping the contaminant from the air stream and absorbing the contaminant in the substrate solution.

Another object of our invention is to provide an electrochemical cell for rapidly detecting a low concentration of air contamination by producing high signal responses from the cell electrodes by using small substrate solution volumes in the cell and low substrate solution feed rates to obtain high concentration levels of the contaminant in the substrate solution.

Another object of our invention is to provide an electrochemical cell for rapidly detecting a low concentration of air contamination by placing the measuring electrode in the substrate solution in the immediate vicinity of the location of maximum absorption of contaminants from the air or gas stream.

A further object of our invention is to provide an electrochemical cell for rapidly detecting low concentration of air contamination which minimizes thermal drift by means of a compensating network.

A still further object of our invention is to provide an electrochemical cell for rapidly detecting low concentration of air contamination when the cell is at any angular attitude or completely inverted.

Other objects of our invention will be obvious from the specification hereinafter set forth.

FIG. 1 shows the effect of varying shunt resistance at the 75°F. base line and at 125°F.

FIG. 2 shows how the zero offset, amount of adjustment to cell potentiometer to attain cell zero setting, varies with temperature variation when a 220KΩ resistor is used in the conventional manner instead of components 1 and 2 in FIG. 6.

FIG. 3 shows how the EMF varies with variation in cyanide concentration at 25°C. both with and without air and oxime present in the cyanide solution when a silver electrode is measured against a standard calomel electrode.

Our invention and FIGS. 1 to 9 will now be described in detail as follows.

Figure 4:
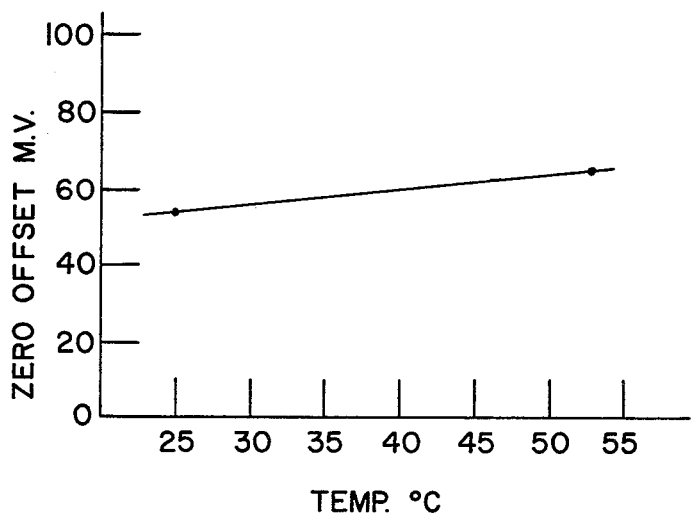
FIG. 4 shows the improvement in zero offset variation with temperature variation over that shown in FIG. 2 when the temperature compensating network of FIG. 6 is used.
Figure 5:
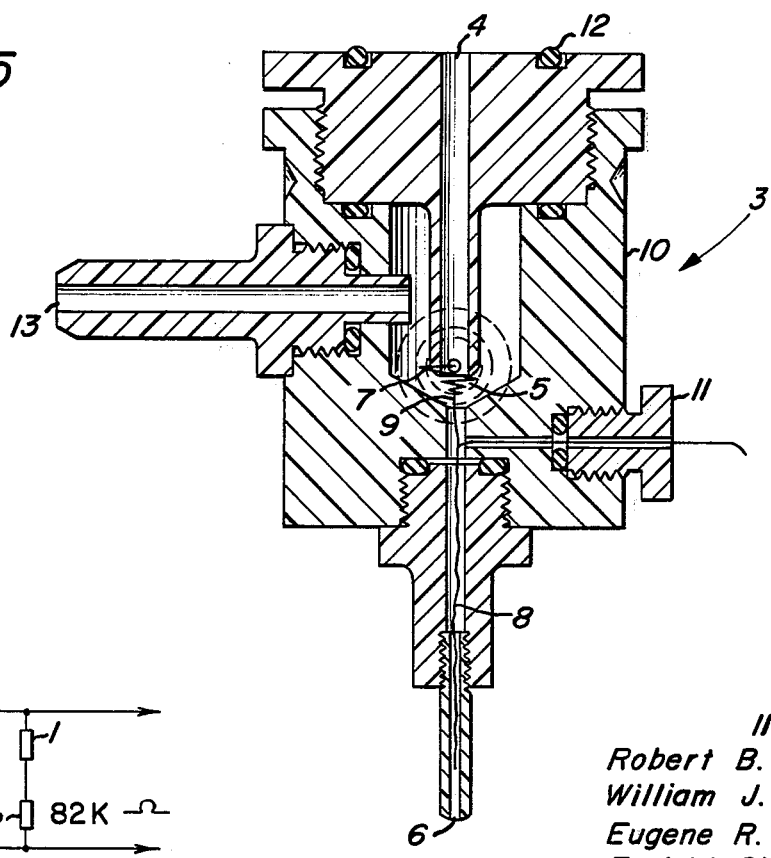
FIG. 5 is a cross sectional view of the electrochemical cell of our invention.
Figure 8:
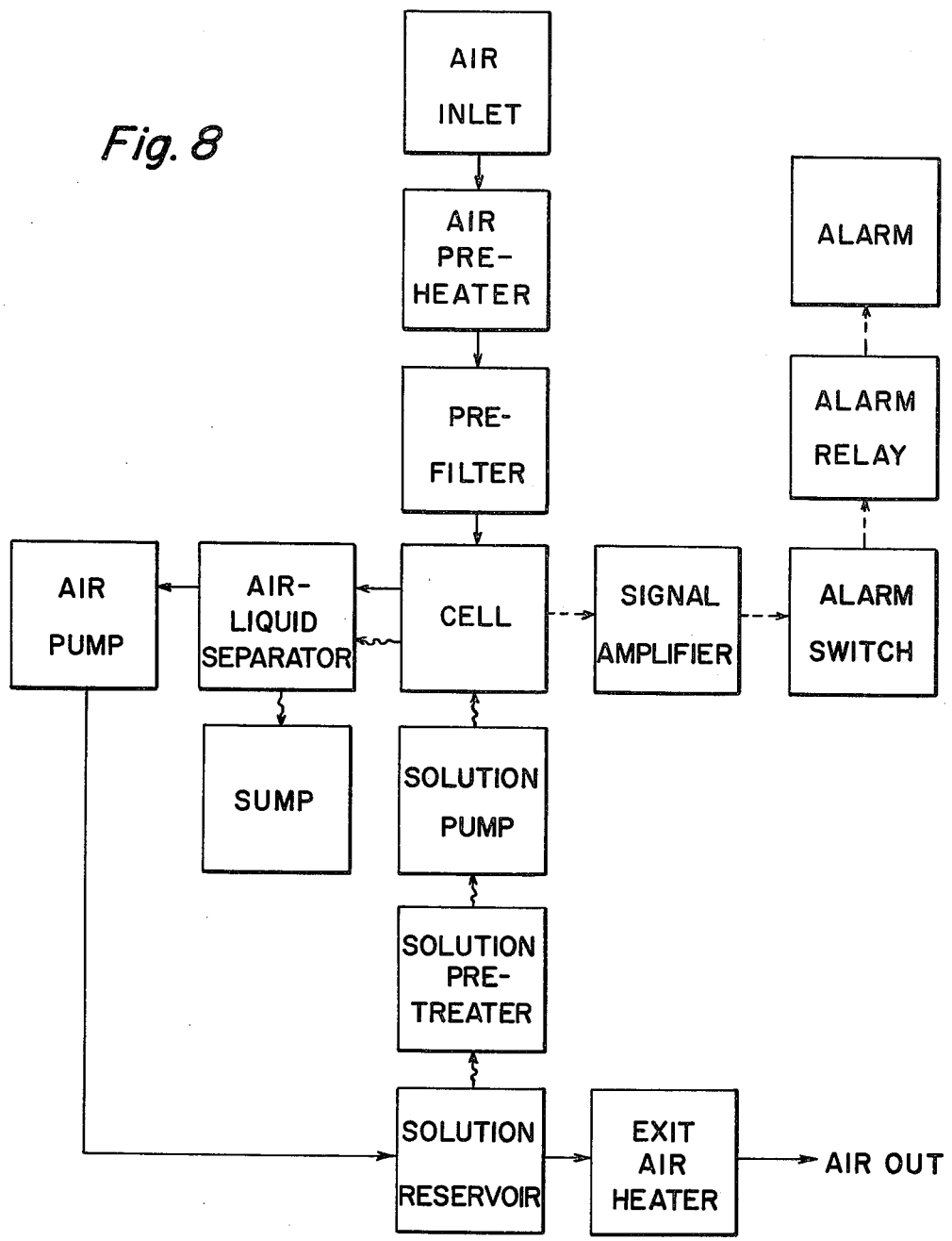
FIG. 8 is a block diagram of the detection system using our cell.
Figure 9:
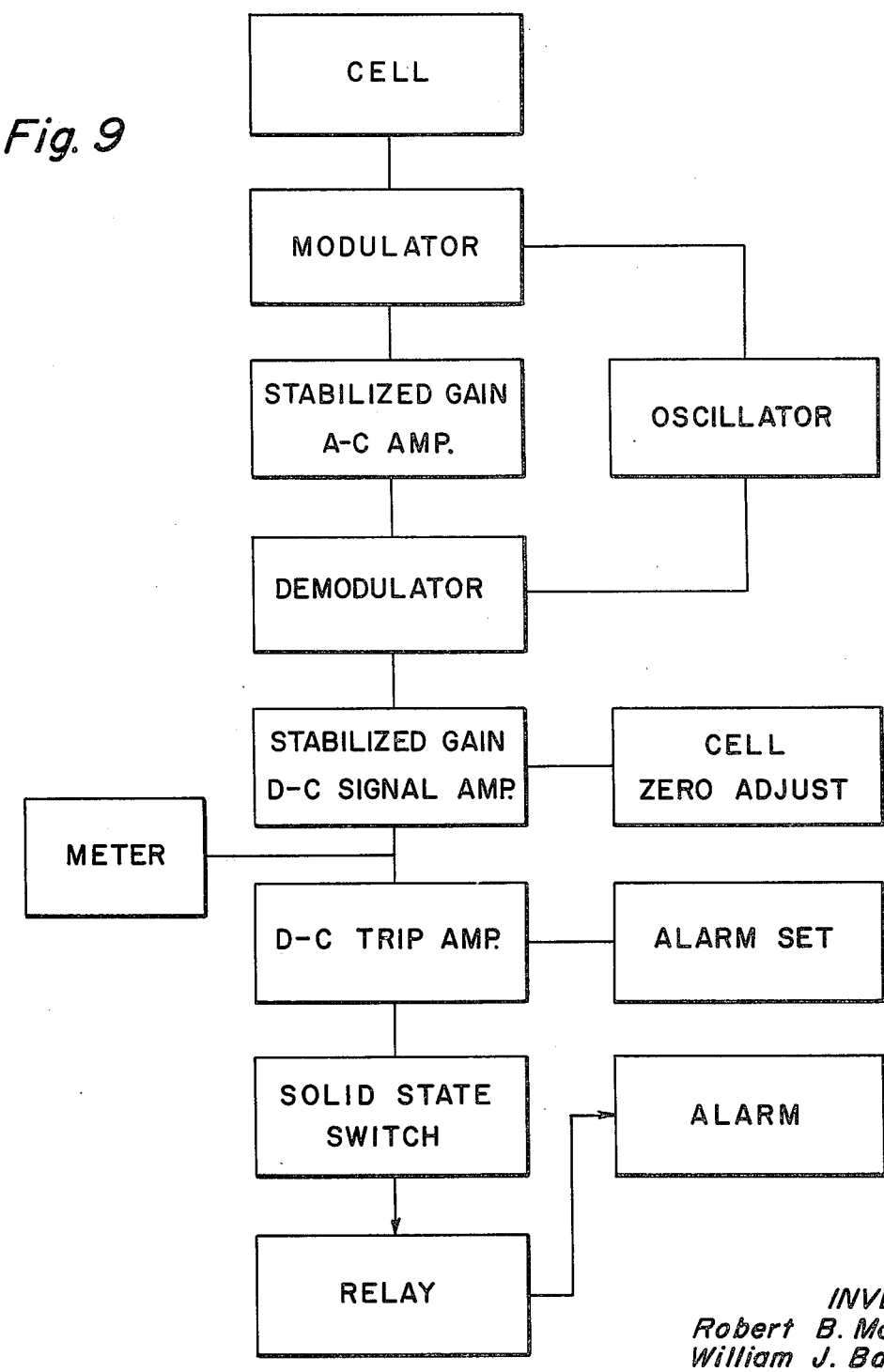
FIG. 9 is a block diagram of the electronic circuitry connected to our cell.

Our cell shown at 3 in FIG. 5, while shown to be made of plastic can also be made of glass. After preheating and prefiltering to remove solids from the air sample, an air sample containing contamination is drawn into an air inlet 4 by a conventional diaphragm type air pump, shown in FIG. 8 of the drawing but not a feature of our invention. Inlet 4 carries the air sample to reaction chamber 5 where it impinges against the chemical substrate solution which is delivered into solution inlet 6 from a conventional reservoir, indicated in FIG. 8, by means of a conventional peristaltic type solution metering pump, indicated in FIG. 8, after the solution has passed through a recycling pretreatment cell for removal of any residual cyanide, or other material which will interfere with the substance being monitored in the air sample and affect detection sensitivity; the pretreatment cell being indicated in FIG. 8. A measuring electrode 7 is located in the vicinity of the solution substrate — air sample interface where the chemical reaction takes place, and reference electrode 8 is located in the solution substrate inlet 6 remote from the air sample — solution substrate interface reaction zone. A fiberglass thread 9 maintains electrolytic contact between the measuring and reference electrodes even in the presence of air bubbles in the solution substrate. Each electrode leadwire is carried outside of the cell body 10 in the conventional manner through compression-type fittings 11 which form leakproof seals. The leadwires are soldered to miniature connector terminals which are located on a cell mounting bracket, not shown in the drawing. Compression type O-ring 12 is used to seal the air passage between the air inlet assembly, which includes the conventional preheater and prefilter unit mentioned above, and the cell body. The reaction at the solution substrate — air sample interface generates an electrical signal which is amplified, by a conventional solid state amplifier, to drive a conventional solid-state switch, none of this circuitry being pertinent to our invention but shown in FIG. 9. The solid-state switch in turn energizes a conventional relay; the relay contacts being used to operate conventional audible and visible alarm devices when our device detects a quantity of a predetermined contaminant in an air stream being monitored. After reaction, the solution substrate containing reaction products is passed through solution outlet 13 to a conventional air-liquid separator, as shown in FIG. 8, and the separated liquid passed to a conventional sump and the separated air with contaminants removed exhausted to the atmosphere. The cycle is then continuously repeated. The utilization of our cell in a detection system is shown in FIG. 8 which is self explanatory. In FIG. 8, solid arrow lines indicate air flow, broken arrow lines electrical signal, and wavy arrow lines solution flow. The electronic circuit to transmit the signal generated by our cell to an alarm is shown in FIG. 9 which is self explanatory. Those of ordinary skill in the detection and electronics art would be well aware as to how to apply the systems shown in FIGS. 8 and 9. Various materials were investigated to determine suitable materials for measuring electrode 7 in FIGS. 5 and 6, and silver and gold were found to give responses related to cyanide concentration. Silver was selected as the preferred measuring electrode material, because it gave better sensitivity; the response and signal generation of the silver electrode for varying cyanide concentration being dramatically demonstrated in FIGS. 3 and 7. After investigation of reference electrode materials, it was determined that the data disclosed that black-platinized platinum, gray-platinized platinum, and platinized titanium demonstrated unchanging, stable potential irrespective of other changes in cell operating conditions and to be suitable as the reference electrode; platinized titanium being preferred. Electrode configuration studies for the measuring electrode were conducted and the results as tabulated in Table 1 on Page 8. The studies disclosed that the measuring electrode configuration was not critical, but configurations 1, 3, and 7 were preferred due to the best combination of short term baseline stability, minimum noise during exposure to toxic compound, and response, as shown in Table 1 (Page 8). Electrolyte, or solution substrate, studies resulted in isonitrosobenzoylacetone oxime solution being preferred. The electrolyte solution has the composition as follows:

0.75 grams of isonitrosobenzoylacetone oxime
1.00 gram of $Na_2B_4O_7 \cdot 10\ H_2O$
0.25 gram of KOH
100 ml of distilled water The procedure to be followed in preparing the electrolyte solution is as follows:

EFFECTS OF THE MEASURING ELECTRODE CONFIGURATION ON CELL PERFORMANCE

| No. | DESCRIPTION OF ELECTRODE | POSITION IN CELL | Short-Term BASELINE NOISE | RESPONSE To 0.20µg/L HCN | NOISE IN OUTPUT DURING HCN TEST |
|---|---|---|---|---|---|
| 1. | 4 TURNS | 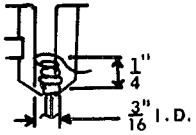 | ±1 mv | 75 mv | ±1 mv |
| 2. | 3 TURNS | 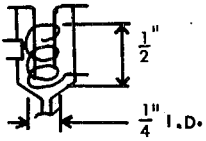 | ±1 mv | 75 mv | ±12 mv |
| 3. | 3 TURNS (Positioned low in absorption chamber) | 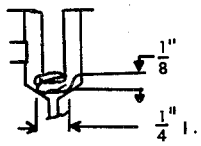 | ±1 mv | 82 mv | ±1 mv |
| 4. | 2⅔ TURNS | 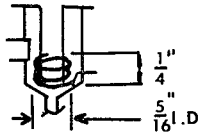 | ±1 mv | 74 mv | ±7 mv |
| 5. | 2⅔ TURNS (Positioned low in cell) | 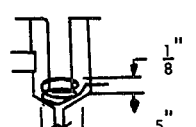 | ±2 mv | 80 mv | ±4 mv |

-continued

EFFECTS OF THE MEASURING ELECTRODE CONFIGURATION ON CELL PERFORMANCE

| No. | DESCRIPTION OF ELECTRODE | POSITION IN CELL | Short-Term BASELINE NOISE | RESPONSE To 0.20µg/L HCN | NOISE IN OUTPUT DURING HCN TEST |
|---|---|---|---|---|---|
| 6. | 3½ TURN SPIRAL STANDARD FORM (Positioned about ⅛ above chamber floor) | | ±2 mv | 77 mv | ±8 mv |
| 7. | 3½ TURN SPIRAL As above, except electrode is pushed to the floor of the chamber | | ±1 mv | 80 mv | ±1 mv |

Note:
THE SAME PIECE OF SILVER WIRE WAS USED FOR EACH OF ABOVE TESTS.

1. Weigh out the solid ingredients.
2. Dissolve the $Na_2B_4O_7 \cdot 10H_2O$ and KOH completely in the required volume of distilled water.
3. Add and dissolve the isonitrosobenzoylacetone oxime.

Figure 6:
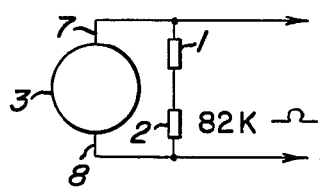
FIG. 6 shows the temperature compensating network to be utilized with our electrochemical cell.
Figure 7:
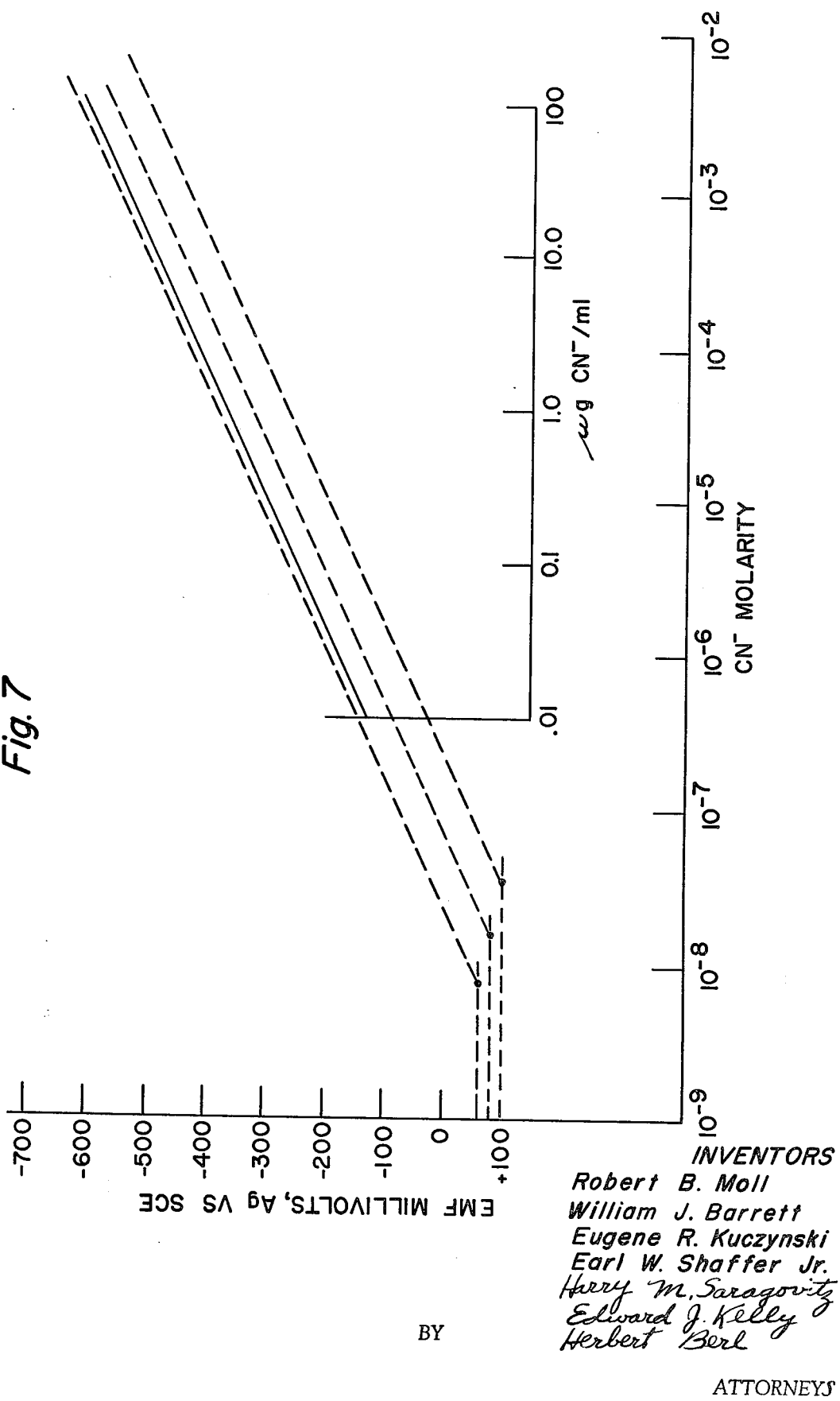
FIG. 7 shows the relationship between cell voltage and cyanide ion molarity for different cyanide concentration at 25°C. when a silver electrode is measured against a standard calomel electrode; the dotted lines being calculated relationships and the solid line representing experimental data obtained in a nitrogen atmosphere.

It is important that the sodium borate and KOH be completely dissolved before the oxime is added, because any undissolved KOH will result in a deep brown color in the vicinity of solid KOH, and the substrate solution will cause a large zero offset and poor sensitivity of the detection system. If the electrolyte solution should evaporate and leave solid oxime crystals, if the detection system is out of operation for a period of time for example, decomposition of the oxime crystals will impair cell performance. Consequently, measures must be taken to avoid formation of oxime crystals and to periodically flush our electrochemical cell to remove any oxime crystals which may form. If the atmosphere being monitored is known to contain only hydrogen cyanide, hydrogen sulfide, or phosgene or these are the only toxic compounds of interest to be monitored it is not necessary to include the isonitrosobenzoylacetone oxime in the electrolyte. When a conventional resistance is utilized in a network with out electrochemical cell in place of components 1 and 2, as shown in FIG. 6, considerable baseline drift is exhibited, as much as 80 mv toward the alarm point, as the temperature is raised from 75° to 125° F. as demonstrated in FIGS. 1 and 2. Such magnitude of drift results in the giving of false alarms. To avoid this problem, the temperature compensating network as shown in FIG. 6 was designed utilizing an 82KΩ resistance 2 and thermistor 1 having a resistance of 190KΩ at 25°C. and 101.3KΩ at 37.8°C. as shown in FIG. 6. Investigation of various materials was conducted to determine a solution substrate additive to reduce water evaporation from the oxime solution and not interfere with detection sensitivity. Of the materials investigated, only ethylene glycol proved to be suitable. While of advantage in reducing water evaporation from the solution, it was found that the ethylene glycol concentration should not be greater than 1.0% by volume of substrate solution, because the cell sensitivity is partially decreased when greater than 1% ethylene glycol is used. Response of a detection system as in FIG. 8 utilizing our electrochemical cell is demonstrated in Table 2 below.

Table 2

DATA ON SYSTEM RESPONSE TO CHEMICAL WARFARE AGENTS

| Agent | Concentration Micrograms/liter air | Time to Alarm (minute) |
|---|---|---|
| GB | 948 | 0.06 |
|  | 10 | 0.22 |
|  | 1.5 | 0.25 |
|  | 0.96 | 0.40 |
|  | 0.3 | 0.51 |
|  | 0.27 | 0.67 |
|  | 0.05 | 0.90 |
| GA | 35 | 0.06 |
|  | 1.6 | 0.25 |
|  | 0.29 | 0.45 |

It is obvious that other modifications can be made of our invention, and we desire our invention to be limited only by the scope of the appended claims.

We claim:

1. An electrochemical cell for continuously and rapidly detecting sub-microgram quantities of toxic compounds irrespective of cell angular attitude comprising a cell body means, a reaction chamber means located within said cell body means, a first inlet means within said cell body means and connecting said reaction chamber means with the environment outside of said cell, a first electrode means within said reaction chamber means adapted to function as a measuring electrode, a second inlet means within said cell body means and connecting said reaction chamber means with an electrolyte reservoir means, a second electrode means within said second inlet means and adapted to function as a reference electrode, fiberglass thread means connecting said first and second electrode means, an outlet means connecting said reaction chamber means with the environment outside of said cell, a temperature compensating means connected across said first and second electrode means and an electrode means adapted to react with said toxic compounds to produce an electrical signal.

2. The electrochemical cell of claim 1 wherein all openings within said cell adjacent to the outside environment are provided with compression type seal means to avoid air leakage into the cell from the outside environment.

3. The electrochemical cell of claim 1 having electroyte pump means for supplying a low volume of electroyte whereby the toxic compounds are detected in the concentration range of $0.2 \times 10^{-6}$ to $0.4 \times 10^{-6}$ grams of toxic compound contaminant per liter of air, said concentration being detected in less than five minutes.

4. The electrochemical cell of claim 1 wherein said first electrode means is made of a material selected from the group consisting of silver and gold.

5. The electrochemical cell of claim 1 wherein said first electrode means is silver.

6. The electrochemical cell of claim 5 wherein said first electrode means is a coiled structure.

7. The electrochemical cell of claim 1 wherein said second electrode means is made of a material selected from the group consisting of black-platinized platinum, gray-platinized platinum, and platinized titanium.

8. The electrochemical cell of claim 1 wherein said second electrode means is platinized titanium.

9. The electrochemical cell of claim 8 wherein said second electrode means is an elongated structure.

10. The electrochemical cell of claim 1 wherein said compensating means consists of an 82KΩ resistance in series with a thermistor having a resistance of 109KΩ at 25°C. and 101.3KΩ at 37.8°C.

11. The electrochemical cell of claim 1 having an electrolyte means consisting of 1.00 grams of $Na_2B_4O_7 \cdot 10H_2O$, 0.25 grams of KOH, and 100 ml of distilled water.

12. The electrochemical cell of claim 11 wherein said electrolyte means contains 0.75 grams of isonitrosobenzoylacetone oxime.

13. The electrochemical cell of claim 12 wherein said electrolyte means contains 1.0% of ethylene glycol by volume of electrolyte solution.

\* \* \* \* \*